United States Patent [19]

Crandall et al.

[11] Patent Number: 4,830,712
[45] Date of Patent: May 16, 1989

[54] PROCESS FOR REFINING ETHYLENE GLYCOL

[75] Inventors: John W. Crandall; Bernard C. Ream, both of Charleston, W. Va.

[73] Assignee: Union Carbide Corporation, Danbury, Conn.

[21] Appl. No.: 102,369

[22] Filed: Sep. 29, 1987

[51] Int. Cl.[4] .......................................... B01D 3/34
[52] U.S. Cl. ...................................... 203/35; 203/3; 203/98; 203/99; 203/DIG. 6; 203/DIG. 19; 203/DIG. 23; 568/868; 568/871
[58] Field of Search ................ 203/3, 91, 94, 98, 99, 203/DIG. 19, DIG. 23, 28, 34, 35, DIG. 6; 568/868, 871, 914, 913, 860

[56] References Cited

U.S. PATENT DOCUMENTS

| | | | |
|---|---|---|---|
| 3,311,544 | 3/1967 | Riehl et al. | 568/871 |
| 3,367,847 | 2/1968 | Pierson | 568/871 |
| 3,408,268 | 10/1968 | Pitts et al. | 203/78 |
| 3,847,754 | 11/1974 | Oliver | 203/35 |
| 4,146,729 | 3/1979 | Goodley et al. | 560/94 |
| 4,225,394 | 9/1980 | Cox et al. | 568/868 |
| 4,358,625 | 11/1982 | Paggini et al. | 568/867 |
| 4,647,705 | 3/1987 | Schmitt et al. | 568/871 |

FOREIGN PATENT DOCUMENTS

| | | | |
|---|---|---|---|
| 0603142 | 8/1960 | Canada | 568/871 |
| 0659339 | 3/1963 | Canada | 568/871 |
| 4111848 | 6/1929 | Japan | 568/871 |
| 1077379 | 7/1967 | United Kingdom | 568/871 |

OTHER PUBLICATIONS

Weissberger et al., "Technique of Organic Chemistry", vol. IV, 2nd ed. 1965 p. 3.

Primary Examiner—David L. Lacey
Assistant Examiner—V. Manohoran
Attorney, Agent, or Firm—Morris N. Reinisch

[57] ABSTRACT

A process is described for recovering polyester-grade ethylene glycol from crude ethylene glycol containing at least one component which has a normal boiling point below that of ethylene glycol, and which can form a UV absorber in the presence of ethylene glycol which comprises supplying to an ethylene glycol distillation system, preferably comprising a fractional distillation zone having an upper portion, a lower portion and an intermediate portion a crude ethylene glycol stream at a determined pH of less than about 7.5; maintaining within the intermediate portion of the fractional distillation zone a diluent having a boiling point below that of the at least one component, such as methanol, at a concentration sufficient to reduce the formation of UV absorber in the intermediate portion wherein at least ethylene glycol, the at least one component and the diluent, are present, and withdrawing ethylene glycol substantially free of the at least one component from the lower portion of the fractional distillation zone.

20 Claims, 6 Drawing Sheets

PROCESS FOR REFINING ETHYLENE GLYCOL

BACKGROUND OF THE INVENTION

1. Field of the Invention

The subject invention is directed to a process for recovering polyester-grade ethylene glycol from crude ethylene glycol, such as the product mixture obtained by hydrogenating dialkyl oxalate.

2. Description of Related Art

The preparation of ethylene glycol is of particular interest to the chemical industry because of the varied uses of this compound. A particularly important use of ethylene glycol is in the production of polyester fibers. Ethylene glycol used in the manufacture of polyester fibers generally must be of exceptionally high purity because even a small quantity of impurity may have a deleterious effect on the resulting polyester fiber. Ethylene glycol also finds application in deicing fluids, antifreeze, hydraulic fluids, and in the manufacture of alkyd resins and solvents.

Ethylene glycol may be prepared by vapor phase catalytic hydrogenation of dialkyl oxalate. This reaction may be represented as shown below:

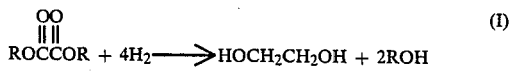

It is believed that hydrogenation of dialkyl oxalate actually proceeds step-wise according to the following two equations:

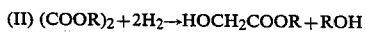

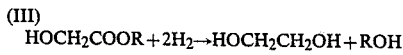

Reference frequently is made herein to the use of dimethyl oxalate (DMO) as the dialkyl oxalate reactant. Since hydrogenation of DMO has been studied in some detail, much of the following discussion describes the behavior of the hydrogenation reaction and subsequent treatment of the hydrogenation product in terms of the hydrogenation of DMO. The following discussion is not, however, intended to be limited to recovery of ethylene glycol formed by DMO hydrogenation.

The ability to increase the purity of ethylene glycol product is of particular interest because impurities, even in small amounts, may render the ethylene glycol unsuitable for manufacturing polyester fiber. When ethylene glycol contains even small quantities of impurities, the properties of the polyester produced, such as fiber dyeing characteristics, fiber strength, fiber color, etcetera, generally are affected adversely. High purity ethylene glycol suitable for use in the product of polyester fiber is referred to as polyester-grade ethylene glycol. Substantially pure ethylene glycol not suitable for use in the production of polyester-grade fiber generally is referred to as antifreeze-grade ethylene glycol.

The product mixture from the hydrogenation of dialkyl oxalate will contain unreacted dialkyl oxalate, partially hydrogenated dialkyl oxalate, i.e., glycolate (HOCH$_2$COOR), alcohol, ethylene glycol and other impurities. For example, in the case of DMO hydrogenation, the product mixture contains ethylene glycol, methanol, unreacted DMO, methyl glycolate (MGA), water, 1,2-butanediol (1,2-BD), various impurities having normal boiling points lower than that of ethylene glycol, and various other impurities having normal boiling points higher than that of ethylene glycol (referred to herein as heavies).

A relatively straightforward process of recovering ethylene glycol from a DMO hydrogenation product mixture employs a three-column purification system wherein the lowest-boiling material such as methanol is removed as overhead in a first fractionation column, while the column bottoms are treated in a second fractionation column where intermediate-boiling materials, such as MGA, DMO, water and 1,2-BD are removed as overhead. Finally, ethylene glycol is recovered by treating the bottoms of the second column in a third fractionation column. In the third column antifreeze-grade ethylene glycol can be recovered in the overhead, polyester-grade ethylene glycol can be recovered in a side stream, and a tails stream comprising heavies is withdrawn from the column bottom.

In order for a sample of ethylene glycol to qualify as polyester-grade ethylene glycol, the sample must pass a stringent ultraviolet light (UV) transmittance test. This test is conducted by comparing the transmittance of ultraviolet light at designated wavelengths through samples of ethylene glycol and of distilled water. The amount of ultraviolet light transmitted through a one centimeter thick ethylene glycol sample, divided by the amount of ultraviolet light transmitted through a sample of distilled water of similar thickness, converted to a percentage, constitutes the percent transmittance of an ethylene glycol sample. Current commercial fiber-grade ethylene glycol ultraviolet light transmittance specifications are listed below:

Ultraviolet Light

| Wave Length (Nanometers) | Percent Transmittance |
|---|---|
| 220 | 70 |
| 275 | 90 |
| 350 | 98 |

The term "UV absorbers" refers to materials which, when present in a sample, reduce the transmittance of ultraviolet light through the sample. Accordingly, the formation of UV absorbers in a process stream results in a decrease of its UV transmittance.

In general, the greater the UV transmittance of an ethylene glycol sample, the greater the value of that ethylene glycol. Therefore, it is preferable that the recovered ethylene glycol not only satisfy the UV transmittance standards identified above but that its UV transmittance be as high as possible. Unfortunately, the above-described three-column refining system typically has not been found to be suitable for recovering polyester-grade ethylene glycol from a crude glycol stream containing substantial quantities of dialkyl oxalate, alkyl glycolate such as DMO and MGA, and other impurities.

DESCRIPTION OF THE INVENTION

Figure 1:
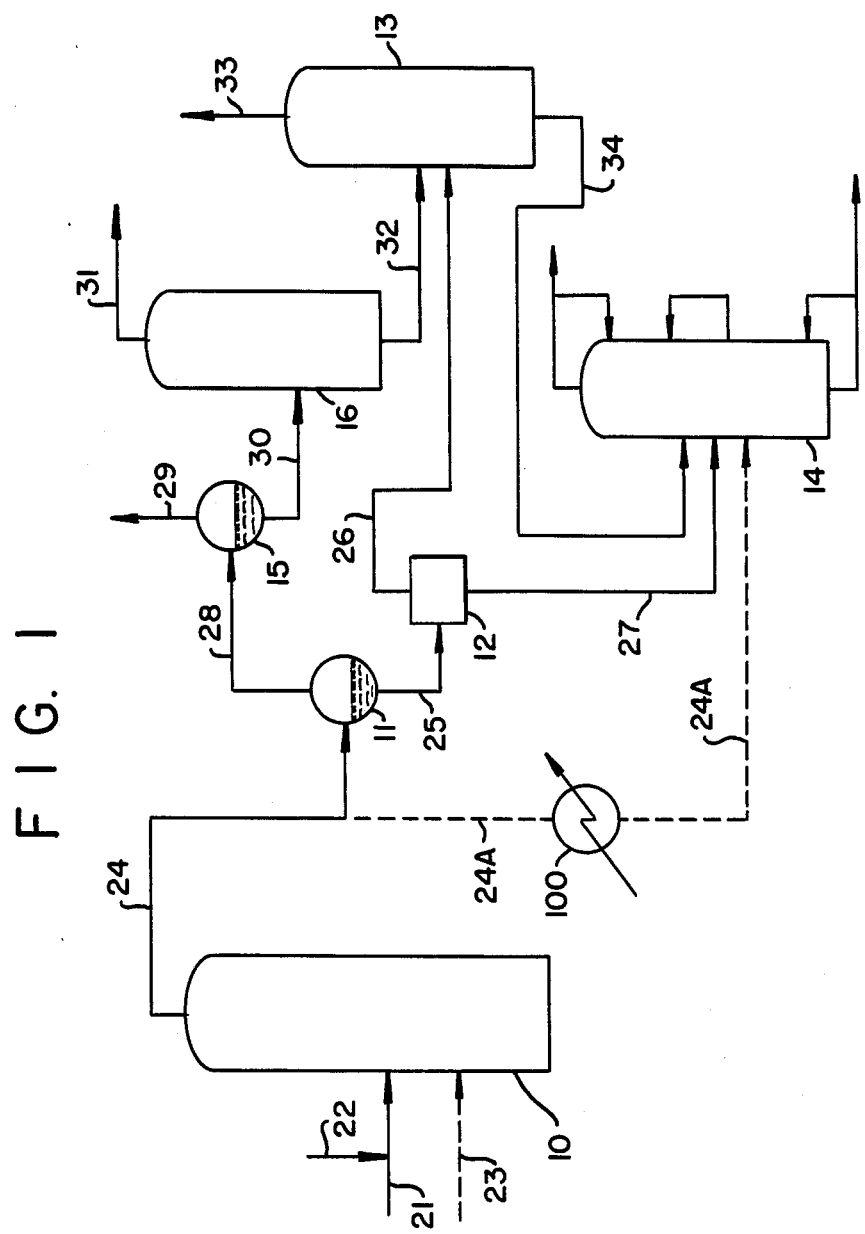
FIG. 1 is a schematic flow chart of a dialkyl oxalate hydrogenation reaction zone and part of a dialkyl oxalate hydrogenation product treatment system.

The present invention is directed to a process for recovering polyester-grade ethylene glycol from crude ethylene glycol. A preferred aspect of the present invention is a process for recovering polyester-grade ethylene glycol from the product mixture obtained by dialkyl oxalate hydrogenation, which mixture typically includes ethylene glycol, substantial quantities of partially hydrogenated dialkyl oxalate, i.e., alkyl glycolate, unreacted dialkyl oxalate, and other impurities.

In accordance with the present invention, a process is provided for recovering polyester-grade ethylene glycol from a crude ethylene glycol stream containing at least one compound which has a normal boiling point below that of ethylene glycol and which can form a UV absorber in the presence of ethylene glycol. The present invention is particularly applicable to recovering polyester-grade ethylene glycol from a crude ethylene glycol stream comprising the product mixture obtained from the hydrogenation of dialkyl oxalate. Such hydrogenation products include ethylene glycol, partially hydrogenated dialkyl oxalate (alkyl glycolate) and unreacted dialkyl oxalate. Other impurities may be present.

It has been determined that the formation of certain UV absorbers from precursors present in crude ethylene glycol recovered from dialkyl oxalate hydrogenation is influenced strongly by the presence or absence of components which in aqueous solution act as bases. In particular, it has been found that the crude ethylene glycol should exhibit a pH, in aqueous solution, of less than about 7.5 if polyester grade ethylene glycol is to be recovered. Thus, a process in accordance with one aspect of the present invention comprises:

(1) supplying to an ethylene glycol distillation system a crude ethylene glycol stream having a determined pH of less than about 7.5; and (2) rectifying said crude ethylene glycol stream and recovering polyester-grade ethylene glycol from said distillation system.

In order to measure the pH of the crude ethylene glycol stream, water first must be added to make an aqueous solution. Generally, the crude ethylene glycol does not contain enough water to measure its pH directly; rather water must be added as part of an analytical procedure to assign a pH to the crude ethylene glycol product. In terms of the present invention, a "determined pH" is the pH of an aqueous solution made using the crude ethylene glycol stream(s) and containing 50 weight percent water. Crude ethylene glycol streams which, in such an aqueous solution, exhibit a pH of less than about 7.5 will hereinafter be referred to as acidic or approximately neutral ethylene glycol.

It also has been found that elevated temperatures during glycol purification, particularly in the presence of certain materials, such as DMO and MGA, facilitate or accelerate the formation of certain UV absorbers deleterious to the UV absorption specifications of ethylene glycol recovered downstream. In the three-column refining system discussed above wherein methanol is removed from the crude ethylene glycol stream via the gaseous overhead withdrawn from the first fractionation column and a bottoms mixture comprising ethylene glycol, DMO and MGA, substantially free of methanol, is supplied to a second fractionation column were relatively high temperatures are needed to separate the DMO and/or MGA from ethylene glycol, formation of such UV absorbers can be to an undesirable extent.

In addition to contributing to unacceptable UV absorption specifications in the ethylene glycol recovered, this three-column distillation arrangement also contributes to substantial loss of ethylene glycol by side reactions. The recovery process of the present invention avoids or reduces these problems and thus permits enhanced recoveries of polyester-grade ethylene glycol.

Therefore, in accordance with another aspect of the present invention, a process is provided for recovering polyester-grade ethylene glycol from crude ethylene glycol containing at least one component which has a normal boiling point below that of ethylene glycol, and which can form a UV absorber in the presence of ethylene glycol, comprising:

(a) feeding the crude ethylene glycol to a fractional distillation zone having an upper portion, a lower portion and an intermediate portion;

(b) in the intermediate portion of the fractional distillation zone, wherein at least ethylene glycol, the at least one component and a diluent having a normal boiling point below that of the at least one component and capable of being at least partially in a liquid phase in said intermediate portion are present, maintaining the diluent at a concentration sufficient to reduce formation of UV absorber in the intermediate portion; and (c) withdrawing ethylene glycol substantially free of the at least one component from the fractional distillation zone.

The process will be better understood with reference to the drawings. Referring to FIG. 1, dialkyl oxalate is fed to hydrogenation reaction zone 10 via line 21. Hydrogen gas preferably is supplied via line 22 into line 21 where it is combined with dialkyl oxalate prior to entering hydrogenation reaction zone 10. Alternatively, hydrogen gas may be supplied directly to hydrogenation reaction zone 10 as a separate feedstream, as represented by dotted line 23.

Hydrogen generally is employed in a stoichiometric excess according to Reaction I, i.e., in a molar amount greater than 4 to 1 relative to dialkyl oxalate, preferably between about 20 to 1 and 135 to 1, most preferably between about 30 to 1 and 70 to 1. In addition, a ballast gas, such as methane or nitrogen, may be provided.

Dialkyl oxalate preferably is supplied as a vapor along with hydrogen, to hydrogenation reaction zone 10. Also, hydrogenation reaction zone 10 preferably is maintained under a condition of temperature and pressure so that the reaction takes place in the vapor phase and condensation of the dialkyl oxalate or product ethylene glycol is prevented. For example, hydrogenation reaction zone 10 typically is maintained at a temperature of from about 140° C. to about 300° C., preferably from about 170° C. to about 260° C., and more preferably from about 180° C. to about 240 °C. The reaction pressure typically can vary from about 0.1 to about 200 atmospheres, and preferably is in the range of from about 1 to about 40 atmospheres. Under such conditions, a typical gas hourly space velocity for zone 10 is in the range of about 180 hr$^{-1}$ to about 360,000 hr$^{-1}$, and preferably is from about 720 hr$^{-1}$ to about 18,000 hr$^{-1}$.

Any suitable hydrogenation catalyst may be employed in zone 10, for example, copper chromite, zinc copper chromite, barium chromite, ammonium copper chromate, zinc chromate, Raney nickel, manganese chromite, or magnesium chromite. Other suitable catalysts comprise compositions of tin, silver, cadmium, ruthenium, zinc, or lead and oxides of chromium of these metals. In general, hydrogenation catalysts containing copper either in its elemental form or combined with oxygen, as well as other hydrogenating metal oxides often employed in conjunction with copper, in supported unsupported form, may be used. Preferred catalysts are reduced copper-zinc chromite catalysts which may be promoted with barium or sodium hydroxide.

Other representative hydrogenation catalysts include zinc, copper, cadmium, chromite catalyst, copper ammonium chromite and zinc chromium oxide, as long as at least some amount of a solid copper-containing catalyst is present. Many suitable copper-containing hydrogenation catalysts are commercially available, such as copper-zinc chromite catalysts, copper barium chromite catalysts, sodium hydroxide-promoted copper chromite, and copper chromite catalysts.

The catalyst may be used in a fixed bed or in a fluid bed and the reaction may be performed either batchwise or continuously, preferably continuously using any suitable reactor design such as a continuous-flow tubular reactor. Since the vapor phase hydrogenation reaction is exothermic, the reactor preferably is cooled to control temperature. Catalyst also may be supported on a carrier, such as active carbon, alumina, silica, diatomaceous earth, pumice, zeolite, or molecular sieve.

A gaseous hydrogenation effluent is withdrawn from hydrogenation reaction zone 10 through line 24. Effluent stream 24 generally comprises a mixture of ethylene glycol, alkanol, unreacted hydrogen, partially hydrogenated and unreacted dialkyl oxalate, and impurities, together with ballast, if employed. The preferred dialkyl oxalates are dimethyl oxalate (DMO) and diethyl oxalate. To simplify the discussion of how the hydrogenation reaction product mixture is purified, the remainder of the process will be described with reference to a hydrogenation effluent stream obtained from the hydrogenation of DMO. The invention is not so-limited, however. The product mixture obtained by hydrogenating diethyl oxalate can be treated in a manner similar to the process described below with reference to the DMO hydrogenation product mixture.

Impurities from the hydrogenation of dimethyl oxalate generally include unreacted DMO, methyl glycolate (MGA), i.e., partially hydrogenated DMO, and other impurities which may be one or more of 2-hydroxymethyl-1,3-dioxolane (HMD), 1,2-butanediol (1,2-BD), water, compounds having a boiling point higher than ethylene glycol, referred to herein as heavies, and compounds having a boiling point lower than ethylene glycol.

Hydrogenation effluent stream 24 preferably is cooled to condense most of its ethylene glycol in condenser 11. The condensate, typically containing ethylene glycol, DMO, MGA, and other impurities, is passed to flash tank 12 via line 25 where it is reduced in pressure, a pressure of about 20 psia is suitable, to yield a vapor stream 26, containing methanol and minor amounts of ethylene glycol and a liquid stream 27, typically containing ethylene glycol, DMO, MGA, and other impurities. Stream 26 is passed to first methanol column 13; while stream 27 is supplied to column 14.

Gaseous stream 28, withdrawn from condenser 11, typically contains methanol, hydrogen and other low boiling material, such as ballast. Gaseous stream 28 is cooled further and passed to second condenser 15, where a vapor stream 29, comprising hydrogen, together with ballast, if employed, and a liquid stream 30, typically comprising methanol and less volatile materials, are withdrawn. Hydrogen stream 29 preferably is recycled to dialkyl oxalate hydrogenation reaction zone 10. Methanol stream 30 is passed to methanol flash pot 16 where it is reduced in pressure, for example, to about 20 psia, and a gaseous stream 31, comprising various low boiling materials which can be vented to the atmosphere, is separated from liquid stream 32, typically comprising methanol, together with minor amounts of various other less volatile materials.

Stream 32 is introduced into first methanol column 13, preferably at a point above the location where the vapor stream 26 is supplied. A high purity methanol product 33 is withdrawn from the top of first methanol column 13; while liquid stream 34, typically comprising methanol and minor amounts of ethylene glycol, DMO, MGA, ethanol, and other impurities, is withdrawn from the bottom. Bottoms stream 34 then is supplied to column 14 preferably at a point above the feed location of liquid stream 27.

Bottoms stream 34 and liquid stream 27 together comprise the crude ethylene glycol stream fed to column 14. In an alternative embodiment, shown in FIG. 1 by dotted line 24A, hydrogenation effluent stream 24 may be cooled in condenser 100 to effect partial condensation and supplied directly to the column 14.

In accordance with the present invention, the crude ethylene glycol stream(s) fed to column 14 should be acidic or approximately neutral. As noted above, it has been found that to avoid the formation of UV absorbers from precursor materials present in the crude ethylene glycol stream during rectification of the crude ethylene glycol, the crude ethylene glycol should exhibit a determined pH, of less than about 7.5. Preferably, the determined pH of the crude ethylene glycol ranges from about 4.0 to about 7.5, and more preferably from about 5.5 to about 7.0.

In general, as the amount of unreacted dialkyl oxalate and partially hydrogenated dialkyl oxalate in a crude ethylene glycol stream is increase, the determined pH of that stream decreases, i.e., the stream becomes more acidic. Conversely, as the amount of unreacted and partially reacted dialkyl oxalate decreases, the determined pH of the stream increases, i.e., the stream becomes more alkaline.

For purposes of this invention the sum of the percentages, by weight, of DMO and MGA in a crude ethylene glycol product mixture obtained by hydrogenating dimethyl oxalate, is referred to as the degree of underhydrogenation. Thus, when DMO is substantially completely hydrogenated, such that the sum of the weight percent of DMO and MGA in the hydrogenation product is less than 0.05, the degree of underhydrogenation is 0.05 or less. The determined pH of such a crude ethylene glycol stream, containing 50 weight percent water, typically would be greater than about 7.5.

It has been found that recovering polyester-grade ethylene glycol which satisfies the above-identified UV transmittance standards from a crude ethylene glycol stream which has a determined pH of above about 7.5, hereinafter referred to as an alkaline ethylene glycol, is much more difficult than from a neutral or acidic crude ethylene glycol stream. While not wishing to be limited to any particular theory, it is believed that some UV absorbers and UV absorber precursors are more volatile and, therefore, more readily separated from ethylene glycol in an acidic environment than in an alkaline environment.

Accordingly, one aspect of the present invention comprises a process wherein the extent of hydrogenation, or alternatively the degree of underhydrogenation, of dimethyl oxalate is controlled so that the crude ethylene glycol stream(s) recovered is acidic or approximately neutral. The degree of underhydrogenation is preferably at least about 0.05, but not more than about 1.0, and more preferably is in the range of from about 0.06 to about 0.5. In this way, adverse effects accompanying an unduly alkaline crude ethylene glycol stream can be avoided. In another aspect of the present invention the pH of an alkaline, crude ethylene glycol stream(s) can be reduced to less than about 7.5 by adding an acid, such as phosphoric acid, to the crude glycol.

Figure 2:
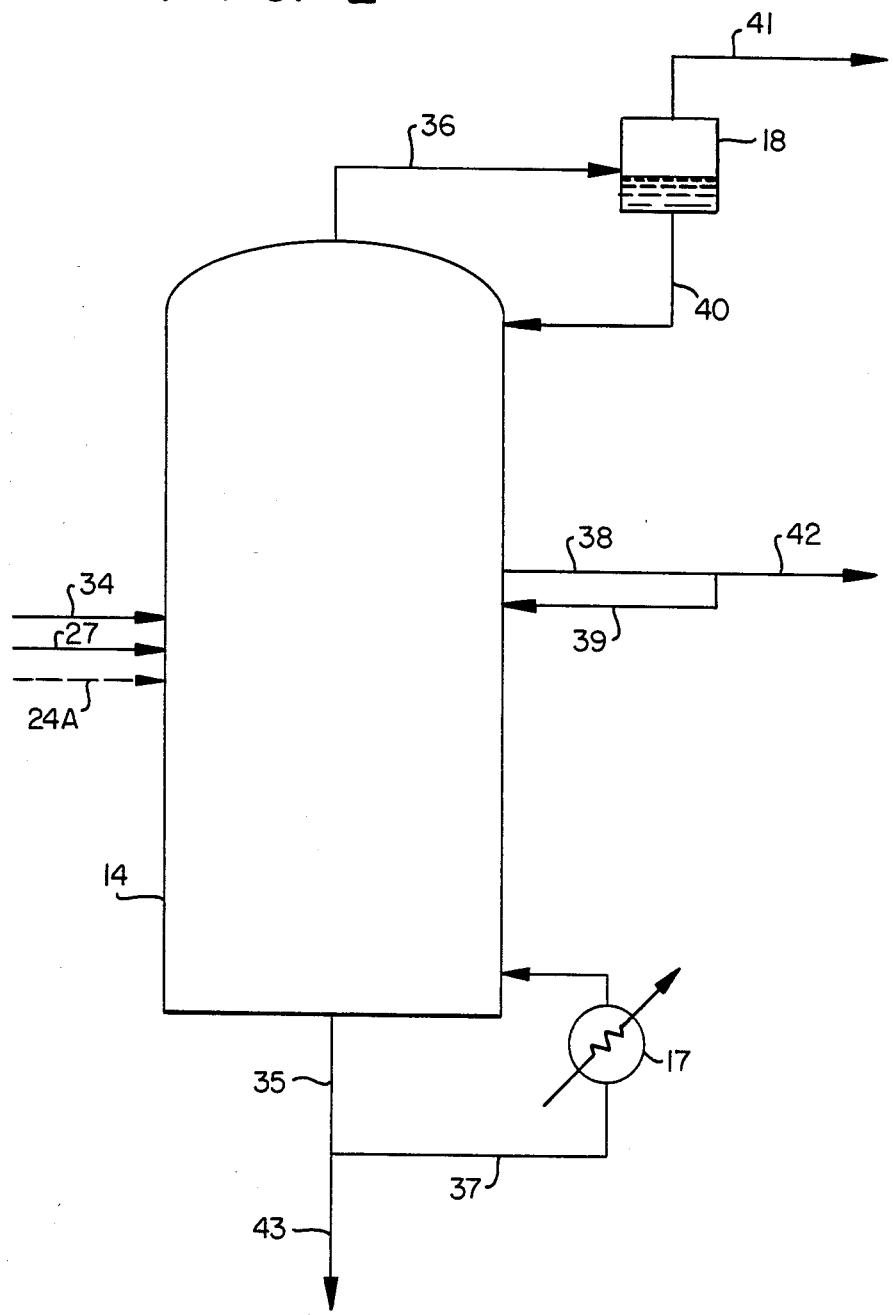
FIG. 2 is a schematic diagram of a rectification column (fractional distillation zone) useful in the ethylene glycol distillation system of the present invention.

Referring now to FIG. 2, a distillation system according to the present invention for refining an acidic crude ethylene glycol stream is illustrated. Column 14 comprises a generally cylindrical column containing trays, packing or a combination of trays and packing for distilling a crude ethylene glycol stream or streams.

In accordance with the present invention, column 14 is operated in such a way that:

(1) light- and intermediate-boiling compounds, e.g., methanol, MGA and DMO, are separated from ethylene glycol in a single column, thereby reducing the consumption of ethylene glycol due to reaction with DMO and/or MGA by minimizing the contact of DMO and/or MGA with ethylene glycol in the absence of methanol;

(2) DMO and MGA are withdrawn from the column in a side stream, which preferably is low in ethylene glycol, thereby reducing the formation of UV absorbers by avoiding the situation where a stream comprising ethylene glycol, together with DMO and/or MGA, is withdrawn from the bottom of the column where elevated temperatures are encountered; and (3) diluent, preferably methanol, is maintained at high concentrations within the column so that a portion of the column where ethylene glycol is present, along with DMO and/or MGA, is operated at a lower temperature than would be the case if the diluent were maintained at a lower concentration.

As noted above, in column 14 a crude ethylene glycol stream(s) is separated into a gaseous overhead methanol stream 41 which is substantially free of ethylene glycol, DMO and MGA, but may contain some ethanol and water, and a tails stream 43, which is substantially free of DMO and MGA, and which contains ethylene glycol and impurities which could be 1,2-BD and heavies. Reflux is supplied to column 14 by partially condensing gaseous overhead stream 36 in partial condenser 18 and returning liquid methanol reflux stream 40 to the top of column 14. Overhead stream 41 is withdrawn from the partial condenser 18. Vapor throughput is generated by vaporizing a portion 37 of liquid bottoms 35 in reboiler 17. The balance of bottoms stream 35, i.e., that which is not vaporized, comprises tails stream 43.

Column 14 typically is operated at a pressure from about 300 to about 800 torr, preferably about 400 torr. At these pressures and under suitable levels of reflux, the temperature at the bottom of column 14 typically will be from about 160° to about 210° C., generally about 180° C. to 200° C., while the temperature at the top of column 14 typically will be from about 50° to about 70° C., generally about 55° C. to 65° C.

Liquid side draw 38, containing DMO and MGA, together with methanol and other impurities, is withdrawn from column 14 at a location in the column above the feed tray(s). Preferably, the location of liquid side draw is chosen so that it contains very little ethylene glycol, preferably less than 20 weight percent, more preferably less than 10 weight percent. A major portion 39 of the liquid side draw 38 is returned to column 14, preferably one tray below the location from which the liquid side draw 38 is withdrawn. The balance of liquid side draw 38, i.e., that which is not returned to column 14, comprises liquid side stream 42. This arrangement facilities the removal of a small purge stream, i.e., side stream 42, from column 14 for removing DMO and MGA from the column.

Column 14 is operated in such a manner that a stream comprising UV absorber-forming material together with diluent and being substantially free of ethylene glycol can be withdrawn from the column. In other words, a "deep cut", comprising low boiling materials, together with intermediate boiling materials, is withdrawn from the column while maintaining the low boiling diluent in a large concentration within the column. In the FIG. 2 embodiment, by properly regulating the level of methanol reflux, substantially all of the DMO and MGA introduced into column 14 with the crude ethylene glycol stream(s) can be withdrawn in a small purge stream 42 from the side of column 14.

Methanol, produced in the hydrogenation of dimethyl oxalate, is the preferred diluent. When methanol is employed as the diluent, it is fed to the column 14 via the crude ethylene glycol stream(s) and as a separate reflux stream. The concentration of diluent within column 14 preferably is maintained at a high concentration by adjusting the reflux ratios in the column. The liquid methanol reflux helps to prevent ethylene glycol from rising to the location from which the liquid side draw 38 is withdrawn and helps to establish a lower temperature profile through the column. As noted above, it is particularly important to maintain lower temperatures in portions of the column where both ethylene glycol and DMO and/or MGA are present in order to avoid formation of UV absorbers. Preferably, by appropriately selecting the column operating pressure and reflux ratios, the temperature in such regions of the column will be maintained below about 160° C., more preferably below about 150° C.

DMO and MGA, supplied to the column 14 via the crude ethylene glycol generally move downward in column 14, encountering progressively greater temperatures, until they are vaporized, after which they move upward with the rising vapor in column 14. At the same time, liquid diluent, preferably methanol, is moving downward in the liquid phase from the top of column 14. Liquid diluent travels downward through the column, coming into contact with and cooling gaseous DMO and MGA moving upward. Gaseous DMO and MGA travel upward, encountering progressively lower temperatures, until they condense, preferably at a location above the location from which the liquid side draw 38 is withdrawn. Liquid diluent travels downward in column 14, encountering progressively greater temperatures, until it is vaporized. It is preferred that internal reflux conditions are maintained such that substantial amounts of liquid diluent pass below the location from which the liquid side draw 38 is withdrawn. Thus, substantial amounts of gaseous diluent, preferably methanol, also pass up through the location from which the liquid side draw 38 is withdrawn, cooling the liquid DMO and MGA at that location and thereby reducing the formation of UV absorbers.

The R/D ratio (the reflux to distillate ratio) of column 14, i.e., the flow rate of the liquid reflux stream 40, by volume, divided by the flow rate of the gaseous overhead stream 41, by volume, preferably ranges from about 0.2 to about 3.0.

The D/F ratio (the distillate to feed ratio) of column 14, i.e, the flow rate of the gaseous overhead stream 41, by volume, divided by the flow rate of the crude ethylene glycol stream(s) fed to column 14, by volume, preferably ranges from about 0.1 to about 0.8.

The IR/LSS ratio (the internal reflux to liquid side stream ratio) of column 14, i.e., the flow rate of internal reflux via line 39, by volume, divided by the flow rate of the liquid side stream 42, by volume, preferably ranges from about 1 to about 50.

The LSS/F ratio (the liquid side stream to feed ratio) of column 14, i.e., the flow rate of the liquid side stream 42, by volume, divided by the flow rate of the crude ethylene glycol stream(s) fed to column 14, by volume, preferably ranges from about 0.01 to about 0.5.

Figure 3:
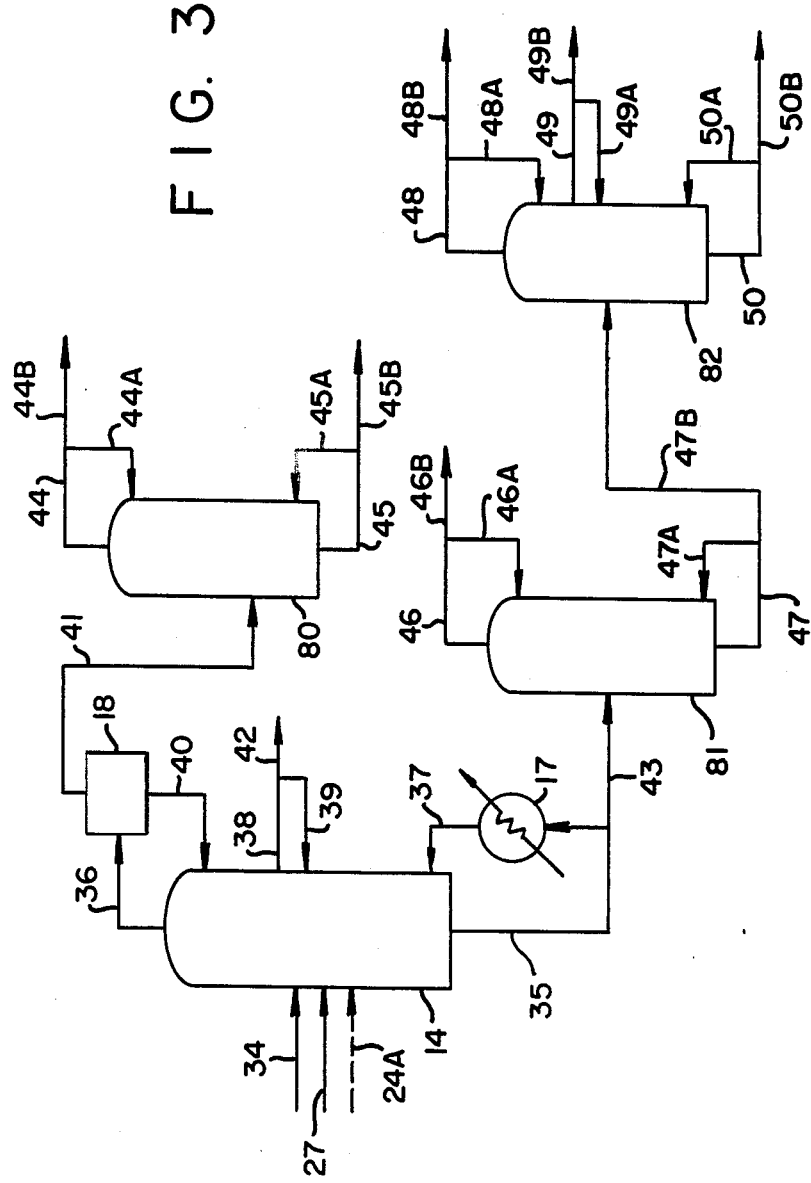
FIG. 3 is a schematic flow chart of a first system for treating a crude ethylene glycol stream or streams which system includes the column of FIG. 2.
Figure 4:
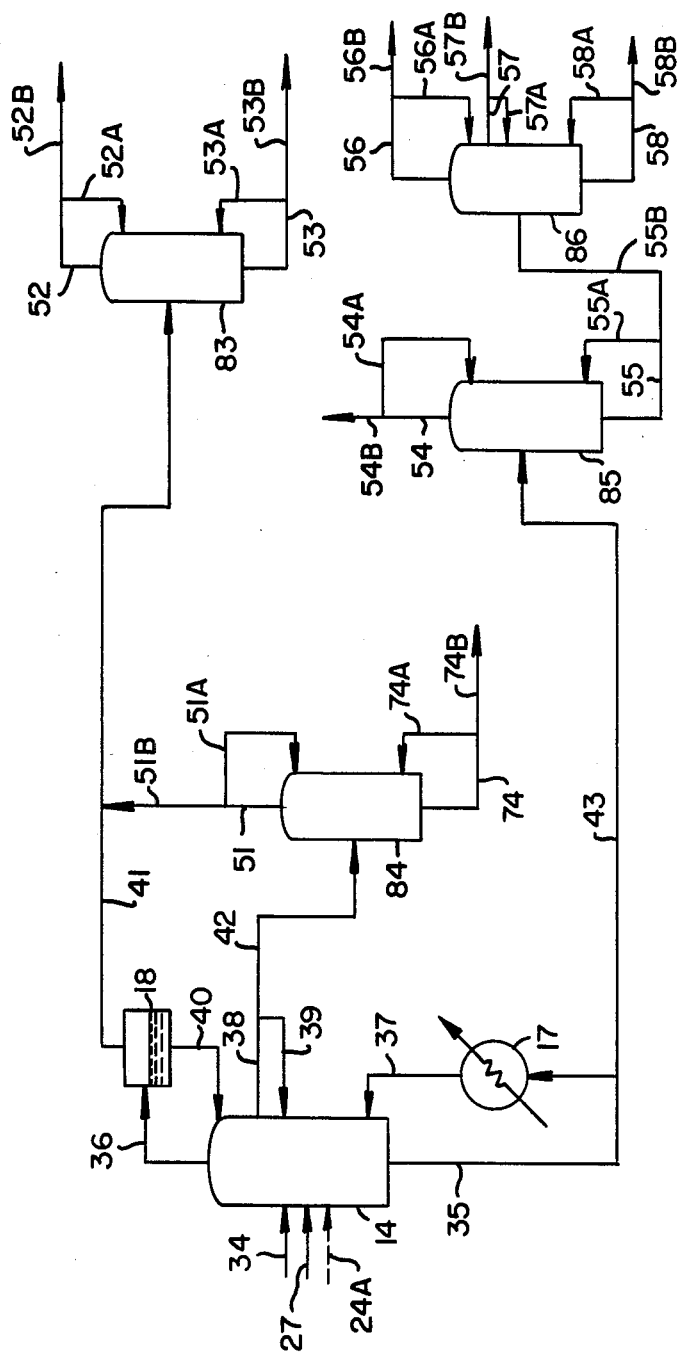
FIG. 4 is a schematic flow chart of a second system for treating a crude ethylene glycol stream or streams which system includes the column of FIG. 2.

Two systems for treating streams withdrawn from column 14 of FIG. 2 are shown in FIGS. 3 and 4. Referring first to FIG. 3, the system for treating the column 14 effluent streams comprises a second methanol column 80, a topping column 81 and a refining column 82.

Gaseous overhead stream 41 is supplied to second methanol column 80, operated at about atmospheric pressure. Stream 41 is rectified to yield an overhead stream 44B, comprising substantially pure methanol, and a bottoms stream 45B, comprising ethanol and water. Reflux for column 80 is provided by partially condensing overhead stream 44 and returning the condensate to the top of column 80 via stream 44A. Heat is supplied to the column by vaporizing a portion 45A of bottoms stream 45.

In the FIG. 3 embodiment, liquid side stream 42 comprising DMO, MGA, and other impurities simply is disposed in any suitable manner.

Tails stream 43, comprising ethylene glycol and impurities which may be 1,2-BD and heavies, is supplied to topping column 81. Ethylene glycol and 1,2-BD form a minimum boiling azeotrope which at 400 torr contains about 55 mole percent 1,2-BD. As such, when the 1,2-BD fed to topping column 81 is removed as an overhead distillate, a portion of the ethylene glycol fed to topping column 81 unavoidably is removed with the 1,2-BD. Liquid bottoms stream 47B, withdrawn from column 81, comprises ethylene glycol and heavies. Reflux for column 81 is supplied by partially condensing overhead azeotrope 46, while heat is supplied by reboiling a portion of bottoms liquid 47.

Bottoms stream 47B, removed from column 81, is supplied to refining column 82. Refining column 82 is operated to produce an overhead stream 48, comprising antifreeze-grade ethylene glycol, a liquid side stream 49, comprising polyester-grade ethylene glycol, and a liquid bottoms stream 50, comprising heavies. Liquid side stream 49 preferably is withdrawn from a location above the location where liquid bottoms stream 47B is supplied to column 82. Reflux is provided to column 82 by partially condensing a portion of the overhead stream 48; while heat is added by vaporizing a portion of the liquid bottoms stream 50.

Normally, the various distillation columns will be thermally integrated as much as possible. For example, gaseous overhead stream 46, withdrawn from topping column 81, and/or gaseous overhead stream 48, withdrawn from refining column 82, may be used to supply heat to the calandria of second methanol column 80.

A second system for treating gaseous overhead stream 41, liquid side stream 42 and tails stream 43 of column 14 is represented in FIG. 4. Referring to FIG. 4, gaseous overhead stream 41, comprising methanol, ethanol and water, is supplied to second methanol column 83, while liquid side stream 42, comprising DMO, MGA, and other impurities, is supplied to a DMO/MGA recovery column 84. Conditions are maintained within DMO/MGA recovery column 84 such that a gaseous overhead system 51B, comprising methanol, ethanol and water, is separated from a liquid bottoms stream 74B, comprising DMO, MGA and other impurities. Overhead reflux and vapor flow through column 84 are provided in a known manner.

Second methanol column 83 is constructed and operated in a manner substantially similar to second methanol column 80 described above in connection with FIG. 3. Thus, a gaseous overhead stream 52B, comprising substantially pure methanol, useful as a methanol source, is separate from a liquid bottoms stream 53, comprising ethanol and water which simply can be disposed.

Tails stream 43 withdrawn from column 14 is supplied to a topping column 85. Topping column 85 is constructed and operated in a manner substantially similar to topping column 81 described above in connection with the FIG. 3 system. Thus, a gaseous overhead stream 54B, comprising 1,2-BD and ethylene glycol, is separated from a liquid bottoms stream 55, comprising ethylene glycol and heavies. Liquid bottoms stream 55B is supplied to a refining column 86.

Refining column 86 is constructed and operated in a manner substantially similar to refining column 82 described above in connection with the FIG. 3 system. Thus, gaseous overhead stream 56B, comprising antifreeze-grade ethylene glycol, is separated from a liquid side stream 57B, comprising polyester-grade ethylene glycol and a liquid bottoms stream 58B, comprising heavies which simply can be disposed.

Again using thermal integration, gaseous overhead stream 54 of topping column 85, and/or gaseous overhead stream 56, withdrawn from refining column 86, may be used to supply heat to the calandria of second methanol column 83.

Figure 5:
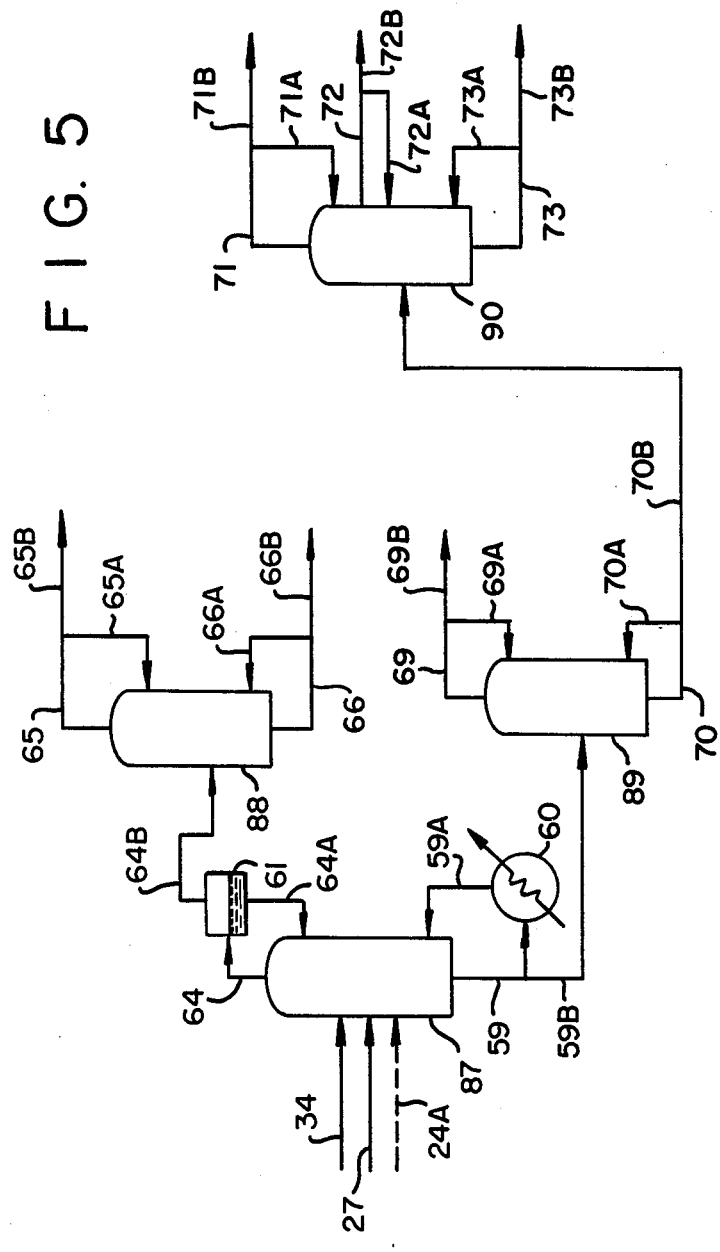
FIG. 5 is a schematic flow chart of a third system for treating a crude ethylene glycol stream or streams.

Another system for treating a crude ethylene glycol stream is shown in FIG. 5. Referring to FIG. 5, column 87 typically comprises a generally cylindrical trayed column or contains packing or a combination of packing and trays. In this embodiment column 87 is operated to separate a liquid bottoms stream 59B substantially free of DMO and MGA, comprising ethylene glycol, 1,2-BD and heavies from a gaseous overhead stream 64B, comprising methanol, MGA, DMO, and other impurities. In other words, in this embodiment, in contrast to column 14 of FIGS. 2-4, the DMO and MGA are driven to the overhead primarily methanolcontaining stream of the crude glycol column 87.

Gaseous overhead stream 64B recovered from column 87 is supplied to second methanol column 88. Second methanol column 88 is operated such that a gaseous overhead stream 65B, comprising substantially pure methanol useful as a source of methanol is separate from a liquid bottoms stream 66, comprising MGA, DMO, and other impurities.

Liquid bottoms stream 59B recovered from column 87 is supplied to topping column 89. Topping column 89 generally is constructed and operated in a manner substantially similar to topping column 81 described above in connection with the FIG. 3 system. Thus, a gaseous overhead stream 69B, comprising the azeotrope of 1,2-BD and ethylene glycol, is separated from a liquid bottoms stream 70B, comprising ethylene glycol and heavies, which is supplied to refining column 90.

Refining column 90 is constructed and operated in a manner substantially similar to refining column 82 described above in connection with FIG. 3. Thus, (1) a gaseous overhead stream 71B, comprising antifreeze-grade ethylene glycol, is withdrawn from the top of column 90, (2) a liquid side stream 72B, comprising polyester-grade ethylene glycol, is withdrawn from an intermediate location of column 9, and (3) a liquid bottoms stream 73B, comprising heavies, is withdrawn from the bottom of the refining column 90.

As in the previous embodiments, gaseous overhead stream 69, withdrawn from topping column 89, and/or gaseous overhead stream 71, withdrawn from refining column 90, may be used to supply heat to the calandria of second methanol column 88 in order to integrate the arrangement thermally.

Figure 6:
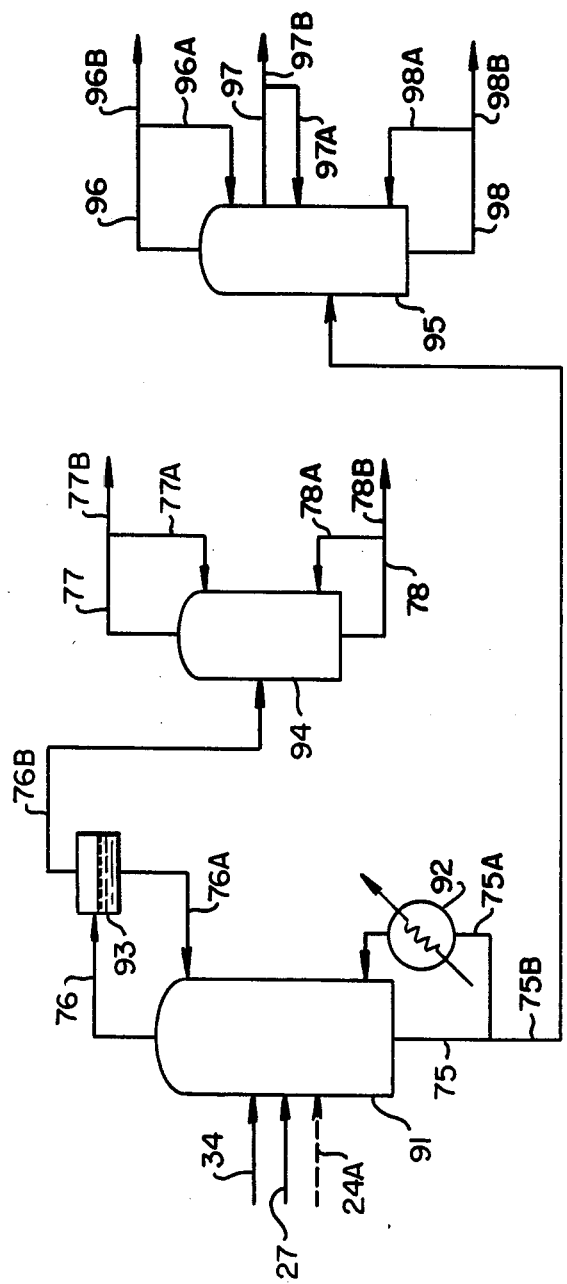
FIG. 6 is a schematic flow chart of a fourth system for treating a crude ethylene glycol stream or streams.

A fourth system for treating crude ethylene glycol stream(s) 24A or 27 and 34 is shown in FIG. 6.

Column 91 of FIG. 6 is operated in a manner similar to column 87 of FIG. 5 such that a liquid bottoms stream 75B, substantially free of DMO and MGA, comprising ethylene glycol and heavies, is separated from gaseous overhead stream 76B, comprising methanol, DMO, MGA, and other impurities. Gaseous overhead stream 76B is supplied to second methanol column 94 wherein it is separated into a gaseous overhead stream 77B, comprising substantially pure methanol, and a liquid bottoms stream 78B, comprising MGA, DMO, and other impurities.

Liquid bottoms stream 75B is supplied directly to a refining column 95. Refining column 95 generally is constructed and operated in a manner substantially similar to refining column 82 described above in connection with the system shown in FIG. 3. Thus, a gaseous overhead stream 96B, comprising antifreeze-grade ethylene glycol, is withdrawn from the top of refining column 85, a liquid side stream 97B, comprising polyester-grade ethylene glycol, is withdrawn from an intermediate location of refining column 95, and a liquid bottoms stream 98B, comprising heavies, is withdrawn from the bottom of refining column 95.

The invention will be better understood by reference to the following examples, which are offered by way of illustration and not limitation.

In all of the following examples, the composition of stream samples was analyzed by gas chromatography (direct injection) on a "SERIES" column (water-free basis). Results for each component are obtained and reported as area percent, which gives a good indication of the relative weight percent of the component in the sample. Water contents were obtained by separate analysis.

EXAMPLES

In the following Examples 1-6, a separation system similar to those illustrated in FIGS. 3 and 4 containing column 14, topping column 81 or 85 and a refining column 82 or 86 was operated to examine the separation of several crude ethylene glycol streams. While the three columns were operated simultaneously, column 14 and the topping column 81/85 were not directly coupled together. Rather, the bottoms stream from column 14 was transferred manually to a graduated feed tank from which it thereafter was pumped into the topping column. The topping and refining columns were coupled together. Due to differences in the operating pressures of the topping and refining columns, the bottoms stream from the topping column was fed to the refining column via an inline solenoid valve operated on a time. All feed tanks were blanketed with nitrogen. Liquid side stream samples from the refining column also were collected under a nitrogen blanket.

Column 14 comprised a 50 millimeter diameter column containing 55 Oldershaw trays, each spaced one inch apart. Column 14 was equipped with a liquid-dividing head operated on a timer for reflux control. A liquid side stream was withdrawn from tray 50 via an inline solenoid valve operated with a timer. In this and all of the following examples, trays are numbered from the bottom of the column to its top. Unless otherwise indicated, the R/D ratio was kept at about 0.5 and the LSS/F ratio was about 0.02. The kettle was provided with an induction tube and an inline solenoid valve for removal of bottoms product. The feed location was tray 30 and a stream preheater was used to preheat the feed controllably before it entered column 14. The feed entered column 14 at a temperature of about 95° C. The column pressure measured at the top of column 14 was about 300 torr. Temperatures measured within the column were about 55° C. at the top, 145° C. at tray 50, 158° C. at tray 30, and 181° C. at the bottom.

The topping column was approximately 2 inches in diameter and 78 inches high and was packed with 0.24 inch PRO-PAK ™ packing. The liquid bottoms stream from column 14 was pumped from a graduated feed tank through a steam preheated and fed at a temperature of about 130° C. to the topping column at a location about 52 inches above the kettle. The pressures measured at the top and the bottom of the topping column were about 400 and about 408 torr, respectively. Temperatures within the topping column were about 169° C. at the top, 177° C. at a location 52 inches above the kettle, and 178° C. at the bottom.

The topping column was equipped with a liquid-diving head operated on a time for reflux control. Unless otherwise noted, the R/D ratio of the topping column was about 15. Bottoms product was removed via an inline solenoid value was fed directly to the refining column by maintaining a pressure differential between the two stills.

The refining column contained 35 Oldershaw trays. The liquid bottoms stream from the topping column was fed at a temperature of about 168° C. to the 10th tray of the refining column. Liquid-dividing heads (operated on timers for reflux control) were located at tray 35 and tray 25 for removal of gaseous overhead and a liquid side stream, respectively. The 10 trays below the feed point were 50 millimeters in diameter with 1 inch spacing, while the rest of the column contained 28 millimeter diameter trays at 1 inch spacings. The kettle was equipped with an induction tube and solenoid valve for removing a liquid bottoms stream.

The pressures measured within the refining column were about 200 torr at the top and 235 torr at the bottom, while the temperatures were about 156° C. at the top, 158° C. at tray 25, 161° C. at tray 10, and 235° C. at the bottom. Unless indicated differently, the refining column was operated with an R/D ratio of about 10.0, a D/F ratio of about 0.1, an IR/LSS ratio of about 1.0, and a LSS/F ratio of about 0.8.

In Examples 1 through 4, four crude ethylene glycol feedstreams comprising dimethyl oxalate hydrogenation reaction products were fed to column 14. The pH of the various feedstreams were fixed by varying the extent of hydrogenation, i.e., the degree of underhydrogenation, in the hydrogenation reactor. In Examples 5 and 6 the pH of the Example 4 feedstream was altered by the addition of acid and base, respectively.

Laboratory operation of the distillation system is typically confined to an eight-hour shift. The columns are lined out and then a timed run is made in which samples are collected, weighted and analyzed. The operating period for timed runs is generally one or two hours.

For Example 2, and also for Example 3, the columns were continuously operated for sixteen hours. These extended runs were made to test the stability of the system to determine if impurities would build up over longer operating times. Three 3 hour timed runs were made during each sixteen hour shift. Examples 2 and 3 were three hour timed runs made in a sixteen hour shift.

During the sixteen hour runs, the columns operated very smoothly and required very little operator attention. Also, no unusual buildup of impurities was observed in the samples collected during the timed runs.

EXAMPLE 1

The compositions of the various selected streams are reported below in Table 1. The weight percentages of MGA and DMO in the feedstream were 0.04 and negligible, respectively, inferring a degree underhydrogenation of 0.04. The determined pH of the feedstream was 8.7. The UV transmittances of the liquid side stream from the refining column were 99.3, 88.4, and 63.6 percent, at wavelengths of 350, 275, and 220 nanometers, respectively, i.e., the product ethylene glycol stream did not meet the polyester-grade ethylene glycol UV transmittance specifications for either the 275 or 220 nm wavelengths.

TABLE 1

| Component | Stream Compositions (area %) | | | | |
|---|---|---|---|---|---|
| | Feed | Col. 14 Side Stream | Col. 14 Bottoms | Topping Col. Bottoms | Refining Col. Side Stream |
| Water | 4.10 | 0.57 | 0.06 | 0.18 | 0.04 |
| Methanol | 23.91 | 1.27 | — | — | — |
| Ethanol | 2.57 | 0.13 | — | — | — |
| Dimethyl Oxalate | — | — | — | — | — |
| Methyl Glycolate | 0.04 | 0.04 | — | — | — |
| Ethylene Glycol | 64.64 | 65.34 | 96.14 | 98.99 | 99.63 |
| 1,2-Butanediol | 2.67 | 13.56 | 2.91 | 0.17 | 0.09 |
| Others | 2.35 | 13.40 | 1.25 | 0.84 | 0.15 |

EXAMPLE 2

The laboratory system used in Example 2 was the same as that in Example 1. The system was operated in substantially the manner described in Example 1 except that, in Example 2, the column pressure measured at the top of column 14 was about 400 torr, and the R/D ratios in column 14 and the topping column were about 1.0 and 120, respectively.

The compositions of the various streams in Example 2 are listed below in Table 2. The weight percentages of MGA and DMO in the feedstream were 0.15 and negligible, respectively, giving a degree of underhydrogenation of 0.15. The determined pH of the feedstream was 6.57. The UV transmittances of the liquid side stream from the refining column were 100.8, 96.1, and 74.5 percent, at wavelengths of 350, 275, and 220 nanometers, respectively, i.e., the product ethylene glycol stream met the polyester-grade ethylene glycol UV transmittance specifications.

TABLE 2

| Component | Stream Compositions (area %) | | | | |
|---|---|---|---|---|---|
| | Feed | Col. 14 Side Stream | Col. 14 Bottoms | Topping Col. Bottoms | Refining Col. Side Stream |
| Water | 1.71 | 8.02 | 0.06 | 0.05 | 0.05 |
| Methanol | 20.76 | 5.53 | — | — | — |
| Ethanol | 0.89 | 0.28 | — | — | — |
| Dimethyl Oxalate | — | — | — | — | — |
| Methyl Glycolate | 0.15 | 3.47 | — | — | — |
| Ethylene Glycol | 75.71 | 49.70 | 98.65 | 99.03 | 99.58 |
| 1,2-Butanediol | 0.90 | 11.65 | 0.95 | 0.36 | 0.32 |
| Others | 0.67 | 22.69 | 0.50 | 0.52 | 0.06 |

EXAMPLE 3

The laboratory system was operated in substantially the same manner described in Example 2 except that, in Example 3, the R/D ratio in the topping column was about 30.0.

The compositions of the various streams in Example 3 are listed below in Table 3. The weight percentages of MGA and DMO in the feedstream were 0.40 and 0.03, respectively, giving a degree of underhydrogenation of 0.43. The determined pH of the feedstream was 4.55. The UV transmittances of the liquid side stream from the refining column were 100.2, 96.4, and 76.6 percent, at wavelengths of 350, 275, and 220 nanometers, respectively, i.e., the product ethylene glycol stream met the polyester-grade ethylene glycol UV transmittance specifications.

TABLE 3

| Component | Stream Compositions (area %) | | | | |
|---|---|---|---|---|---|
| | Feed | Col. 14 Side Stream | Col. 14 Bottoms | Topping Col. Bottoms | Refining Col. Side Stream |
| Water | 1.93 | 2.70 | 0.05 | 0.05 | 0.06 |
| Methanol | 20.52 | 2.65 | — | — | — |
| Ethanol | 1.26 | 0.19 | — | — | — |
| Dimethyl Oxalate | 0.03 | — | — | — | — |
| Methyl Glycolate | 0.40 | 9.36 | — | — | — |
| Ethylene Glycol | 74.00 | 49.88 | 97.84 | 98.64 | 99.63 |
| 1,2-Butanediol | 1.29 | 10.08 | 1.28 | 0.27 | 0.23 |
| Others | 1.20 | 20.73 | 1.09 | 1.09 | 0.16 |

EXAMPLES 4-6

The laboratory system used in Examples 4-6 was the same as that in Example 1. The system was operated in substantially the manner described in Example 2, except that, in Examples 4–6, the R/D ratio in the topping column was about 60.

The feedstream in Example 4 comprised a portion of a hydrogenation reaction product, other portions of which were pH adjusted and used as the feedstreams in Examples 5 and 6. The pH of the feedstream in Example 4 was about 7.3. For Example 5, a portion of the Example 4 feedstream was pH adjusted from 7.3 to 4.5 by addition of phosphoric acid; while for Example 6, a portion of the Example 4 feedstream was pH adjusted from 7.3 to 9.1 by addition of aqueous sodium hydroxide.

The compositions of the feedstream and the ethylene glycol product streams in Examples 4–6 are listed in Table 4. The UV transmittances of the liquid side stream from the refining column of Example 4 were 100.1, 95.2, and 81.2 percent, at wavelengths of 350, 275, and 220 nanometers, respectively, i.e., the product ethylene glycol stream of Example 4 met the polyester-grade ethylene glycol UV transmittance specifications. The UV transmittances of the liquid side stream from the refining column of Example 5 were 101.2, 96.3 and 76.4 percent, at wavelengths of 350, 275, and 220 nanometers, respectively, i.e., the product ethylene glycol stream of Example 5 met the polyester-grade ethylene glycol UV transmittance specifications. The UV transmittances of the liquid side stream for the refining column of Example 6 were 100.0, 92.4, and 69.4 percent, at wavelengths of 350, 275, and 220 nanometers, respectively, i.e., the product ethylene glycol stream of Example 6 did not meet the polyester-grade ethylene glycol UV transmittance specifications and was clearly inferior to the products of Examples 4 and 5.

TABLE 4

| Component | Feed-Stream | Example 4 Product | Example 5 Product | Example 6 Product |
|---|---|---|---|---|
| Water | 2.18 | 0.18 | 0.32 | 0.34 |
| Methanol | 26.41 | — | — | — |
| Ethanol | 0.07 | — | — | — |
| Methyl Glycolate | 0.04 | — | — | — |
| Ethylene Glycol | 70.10 | 99.78 | 99.68 | 99.65 |
| Dimethyl Oxalate | 0.03 | — | — | — |
| 1,2-Butanediol | 0.41 | 0.04 | — | 0.02 |
| Others | 0.01 | 0.01 | — | — |

Stream Composition (area %)

EXAMPLE 7

A column of the type shown in FIG. 2 in accordance with the present invention, comprising 35 Oldershaw trays having liquid dividing heads located at tray 35 and tray 25 for removal of a gaseous overhead stream and a liquid side stream, respectively, was tested. The feed point was tray 15.

The column was operated at a base temperature of about 201° C. and a head temperature of about 67° C. The column pressure measured at the top of the column was about 760 torr. The temperature of the feedstream was about 25° C. The temperatures at trays 15 and 25 were measured to be about 163° C. and 101° C., respectively. The column was operated with a R/D ratio of about 1.0, a D/F ratio of about 0.55, an IR/LSS ratio of about 10.0, and a LSS/F ratio of about 0.06. The ratios were determined on a volume basis.

A synthetic feed containing 3 percent dimethyl oxalate was used to simulate a crude ethylene glycol stream. The composition of the synthetic feed is shown below in Table 5. Table 5 also shows the compositions of the gaseous overhead stream, the liquid side stream and the liquid bottoms stream, corresponding to the gaseous overhead stream 41, the liquid side stream 42 and the liquid bottoms stream 43 of FIG. 2, respectively.

TABLE 5

Column 14 Composition Profiles Area Percent

| Component | Feed-Stream | Gaseous Overhead Stream | Liquid Side Stream | Liquid Bottoms Stream |
|---|---|---|---|---|
| Water | 2.0 | 2.5 | 16.8 | — |
| Methanol | 47.0 | 94.9 | 31.5 | — |
| Ethanol | 1.0 | 1.9 | 0.8 | — |
| Ethylene Glycol | 47.0 | — | 9.6 | 99.6 |
| Dimethyl Oxalate | 3.0 | 0.3 | 41.1 | 0.3 |

Liquid bottoms withdrawn from column 14 was collected and batch-distilled by charging a 476 milliliter sample to a 35 tray finishing column operating at a head pressure of about 195 torr. The finishing column was operated at total reflux for one-half hour and then 48 milliliters of gaseous overhead (about 10 percent of the charge) was removed from the top of the finishing column, then being operated at an R/D ratio of about 10.0. Gaseous overhead production then was stopped and liquid side stream samples (1–4 in Table 6), each comprising approximately 50 milliliters, were withdrawn from the finishing column at tray 25 while operating at an IR/LSS ratio of about 3.0. Ultraviolet (UV) transmittance measurements were made on the gaseous overhead (after condensation) and on each of four liquid side stream samples, identified as Samples 1 through 4 in Table 6. These UV transmittance measurements are listed in Table 6.

TABLE 6

UV Transmittance Specifications of Gaseous Overhead and Liquid Side Stream Samples Withdrawn from Finishing Column

| Sample | UV Transmittance, Percent | | |
|---|---|---|---|
|  | 350 nm | 275 nm | 220 nm |
| Gaseous Overhead | 57 | 25 | 0 |
| 1 | 100 | 100 | 85 |
| 2 | 100 | 100 | 87 |
| 3 | 100 | 100 | 88 |
| 4 | 100 | 100 | 86 |

As shown in Table 6, all four liquid side stream samples passed the polyester-grade ethylene glycol UV transmittance test. This example demonstrates that the apparatus operated in accordance with the present invention can process fairly impure hydrogenation product and still recover high quality polyester-grade ethylene glycol. In addition, about 80 percent of the dimethyl oxalate present in the feedstream to column 14 was recovered in the liquid side stream withdrawn from the column.

EXAMPLE 8

In this example, the synthetic feed contained both dimethyl oxalate and methyl glycolate (see Table 7). The columns used in Example 7 were used again in Example 8. Column 14 was operated under conditions similar to those in Example 7 with the exception that, in this example, the head temperature was maintained at about 66° C., the D/F ratio, by volume, was about 0.57, and the LSS/F ratio, by volume, was about 0.07.

TABLE 7

Column 14 Composition Profiles Area Percent

| Component | Feed-Stream | Gaseous Overhead Stream | Liquid Side Stream | Liquid Bottoms Stream |
|---|---|---|---|---|
| Water | 2.61 | 3.04 | 12.93 | 0.11 |
| Methanol | 56.48 | 94.90 | 21.29 | — |
| Ethanol | 1.00 | 1.73 | 0.51 | — |
| Methyl Glycolate | 1.86 | — | 44.21 | — |
| Ethylene Glycol | 35.35 | — | — | 97.10 |
| Dimethyl Oxalate | 1.64 | 0.07 | 19.89 | 0.03 |
| 1,2-Butanediol | 0.89 | — | 0.02 | 2.58 |

This test proved successful as essentially all of the methyl glycolate and 84 percent of the dimethyl oxalate were recovered in the liquid side stream of the column.

EXAMPLE 9

In this example, a crude ethylene glycol stream was fed to a column substantially corresponding to column 14 of FIG. 2 having 40 Oldershaw trays. Column 14 was operated at about atmospheric pressure. Liquid dividing heads were located at tray 40 and at tray 30 for removal of a gaseous overhead stream and a liquid side stream, respectively. A feedstream was introduced to the column at tray 10. The feedstream, representative of a dimethyl oxalate hydrogenation product, contained 8.93 percent dimethyl oxalate and 7.08 percent methyl glycolate.

Column 14 was operated at a bottom temperature of about 204° C., and an overhead temperature of about 65° C. The feed temperature was about 25° C. The R/D ratio was maintained at about 1.0. The IR/LSS ratio was adjusted to maintain the temperature at tray 30 at approximately 118° C., 119° C. at tray 17 and 160° C. at tray 10. The IR/LSS ratio was maintained at about 2.2 and the D/F and LSS/F ratios were maintained at about 0.42 and 0.19, respectively.

The conditions within the column were maintained so as to (a) minimize the amount of ethylene glycol in the gaseous overhead stream and in the liquid side stream, and (b) ensure that most of the dimethyl oxalate and methyl glycolate, along with some methanol, were removed via the liquid side stream.

The compositions of the streams withdrawn from the column, i.e., the gaseous overhead stream, the liquid side stream and the liquid bottoms stream, are shown in Table 8. As shown by these results, 99.3 percent of the methyl glycolate and 60 percent of the dimethyl oxalate contained in the feedstream were recovered in the liquid side stream.

TABLE 8

Column 14 Composition Profiles Area Percent

| Component | Feed-Stream | Gaseous Overhead Stream | Liquid Side Stream | Liquid Bottoms Stream |
|---|---|---|---|---|
| Water | 2.04 | 2.17 | 7.19 | 0.19 |
| Methanol | 47.11 | 94.29 | 18.71 | 0.12 |
| Ethanol | 0.84 | 1.68 | 0.57 | — |
| Methyl Glycolate | 7.08 | 0.19 | 37.02 | — |
| Ethylene Glycol | 29.63 | — | 1.30 | 90.29 |
| Dimethyl Oxalate | 8.93 | — | 28.35 | 0.41 |
| 1,2-Butanediol | 0.25 | — | — | 0.82 |

TABLE 8-continued

Column 14 Composition Profiles Area Percent

| Component | Feed-Stream | Gaseous Overhead Stream | Liquid Side Stream | Liquid Bottoms Stream |
|---|---|---|---|---|
| Others | 3.85 | 1.65 | 6.86 | 8.19 |

EXAMPLE 10

In the example, the feed mixture consisted of a dimethyl oxalate hydrogenation product having a composition approximately as shown as stream A in Table 9. The hydrogenation product was supplied to a condenser in which a portion of the hydrogenation product mixture was condensed. A vapor stream consisting primarily of methanol was withdrawn from the condenser and disposed. The liquid stream withdrawn from the condenser was supplied as a crude ethylene glycol stream to a column substantially corresponding to column 91 of FIG. 6. The column was coupled to and operated integrally with a refining column substantially corresponding to refining column 95 of FIG. 6.

This apparatus was operated for several days during which no bottoms product was removed (except for analysis) from the refining column. After lineout, the columns were operated for a timed run of four hours.

Column 91 was packed with PRO-PAK ™ protruded packing and was estimated to contain 60 theoretical plates. The crude ethylene glycol stream was introduced at about theoretical plate 40. The column was operated at a bottom temperature of about 178° C., a head temperature of about 67° C., and a pressure of about 400 torr. The temperature of the crude ethylene glycol stream entering the column was about 100° C. Temperature was controlled throughout the column by adjusting the reflex to maintain a temperature of about 158° C. at the feed point. The R/D ratio was about 1.5.

A gaseous overhead stream (stream B in Table 9), corresponding to the gaseous overhead stream 76B in FIG. 6, and a liquid bottoms stream (stream C in Table 9), corresponding to the liquid bottoms stream 75B in FIG. 6, were withdrawn from the column.

The refining column contained 35 Oldershaw trays with liquid dividing heads at trays 35 and 25 to remove the gaseous overhead stream (stream D in Table 9), corresponding to the gaseous overhead stream 96B in FIG. 6 and comprising antifreeze grade ethylene glycol, and the liquid side stream (stream E in Table 9), corresponding to the liquid side stream 97B in FIG. 6 and comprising polyester-grade ethylene glycol. The feed to the refining column consisted of the bottoms product from column 91 and was introduced at tray 15 of the refining column at a temperature of about 160° C. The refining column was operated with a bottom temperature of about 172° C., a head temperature of about 165° C., and a column pressure of about 200 torr measured at the top of the column. The temperature was maintained at about 166° C. at tray 25 and about 168° C. at tray 15. The R/D ratio was about 20.0 and the IR/LSS ratio was about 1.0.

Ultraviolet transmittance tests of streams A, D and E are reported in Table 10.

TABLE 9

| | Composition Profiles Area Percent | | | | |
|---|---|---|---|---|---|
| Component | A | B | C | D | E |
| Water | 1.83 | 3.09 | 0.28 | 1.00 | 0.09 |
| Methanol | 52.82 | 86.80 | 0.05 | 0.07 | 0.14 |
| Ethanol | 1.12 | 2.14 | — | — | — |
| Methyl Glycolate | — | — | — | — | — |
| Ethylene Glycol | 44.70 | 8.56 | 99.12 | 97.91 | 99.65 |
| 1,2-Butanediol | 0.95 | 1.57 | 0.25 | 1.23 | 0.18 |
| Others | 0.41 | 0.91 | 0.58 | 0.79 | 0.04 |

TABLE 10

| | Ultraviolet Transmittance, Percent | | |
|---|---|---|---|
| Sample | 350 nm | 275 nm | 220 nm |
| Stream A | 99.6 | 87.7 | 28.1 |
| Stream D | 96.4 | 37.0 | 10.7 |
| Stream E | 100.0 | 96.6 | 81.3 |

EXAMPLE 11

In this example a staged three-column apparatus, such as the one discussed in the Background Of The Invention section, was tested. A hydrogenation product (stream A in Table 11) was fed to a first distillation column containing 50 Oldershaw trays. The first distillation column was operated at a base temperature of about 161° C., a head temperature of about 62° C., and a column pressure measured at the top of the column, of about 760 torr. The R/D ratio was maintained at about 2.0. The temperature of the feedstream entering the first distillation column at tray 20 was about 25° C. The temperature in the first distillation column at tray 20 was maintained at about 68° C. The D/F mass ratio was about 0.51.

A first overhead stream comprising methanol was withdrawn from the first distillation column and a first bottoms stream (stream B in Table 11), comprising ethylene glycol, water, ethanol, and other impurities was withdrawn from the bottom of the column.

A second distillation column comprised a packed column containing about 60 theoretical plates. The first bottoms stream was introduced into the second distillation column at about theoretical plate 40 at a temperature of about 150° C. The second distillation column was operated at a base temperature of about 177° C., a head temperature of about 141° C., and a pressure of about 400 torr. The R/D ratio was maintained at about 15.0. The temperature in the second distillation column at theoretical plate 40 was maintained at about 158° C. A second overhead stream, comprising impurities, intermediates and some ethylene glycol, was withdrawn from the top of the second distillation column. A second bottoms stream (stream C in Table 11), comprising ethylene glycol and heavies, was withdrawn from the bottom of the second distillation column. The second bottoms stream was introduced into a third distillation column.

The third distillation column contained 35 Oldershaw trays and was operated at a base temperature of about 172° C., a head temperature of about 166° C. and a column pressure measured at the top of the column of about 200 torr. The second bottoms stream was introduced into the third distillation column at tray 15 at a temperature of about 170° C. Liquid dividing heads were located at trays 35 and 25 to remove an overhead ethylene glycol stream (stream D in Table 11) and a polyestergrade ethylene glycol side stream (stream E in Table 11), respectively. The temperatures at trays 15 and 25 were maintained at about 168 and 167° C., respectively. The R/D and IR/LSS ratios were maintained at about 10.0 and 1.0, respectively. A third bottoms stream also was withdrawn from the bottom of the third distillation column.

TABLE 11

| | Composition Profiles Streams of a Conventional Three-Column Apparatus Area Percent | | | | |
|---|---|---|---|---|---|
| Component | A | B | C | D | E |
| Water | 1.30 | 2.60 | 0.15 | 0.44 | 0.08 |
| Methanol | 54.60 | 0.09 | 0.07 | 0.09 | 0.09 |
| Ethanol | 0.97 | 2.33 | — | — | — |
| Methyl Glycolate | 0.10 | — | — | 0.02 | — |
| Dimethyl Oxalate | 0.10 | — | — | — | — |
| Ethylene Glycol | 43.10 | 94.17 | 99.22 | 98.08 | 99.61 |
| 1,2-Butanediol | 0.91 | 2.12 | 0.18 | 1.19 | 0.18 |
| Others | 0.78 | 1.55 | 0.53 | 0.38 | 0.03 |

The results of an ultraviolet transmittance test on stream E in Table 11—the polyester-grade ethylene glycol stream—are reported below in Table 12. The product does not satisfy the previously stated transmittance standards.

TABLE 12

| | Ultraviolet Transmittance, Percent | | |
|---|---|---|---|
| Sample | 350 nm | 275 nm | 220 nm |
| Stream E | 100.0 | 76.7 | 64.8 |

EXAMPLE 12

In this example an apparatus substantially corresponding to that shown in FIG. 3 was employed including a column 14, a topping column 81 and a refining column 82. Column 14 consisted of 55 Oldershaw trays. Liquid dividing heads were located at trays 55 and 50 for removal of a gaseous overhead stream and a liquid side stream, respectively. The feed point was tray 30. Column 14 was operated at a base temperature of about 181° C., a head temperature of about 57° C., and a column pressure measured at the top of the column of about 400 torr. The temperature of the feed entering column 14 was about 100° C. The temperature at tray 30 of the column was maintained at about 160° C. and the temperature at tray 50 of the column was maintained at about 142° C. An R/D ratio of about 1.0, a D/F ratio of about 0.23 and an LSS/F ratio of about 0.027 were maintained in the column. These ratios were determined on a volume basis.

The composition of the material fed to column 14 is listed in Table 13 under stream A. A gaseous overhead stream consisting primarily of methanol, a liquid side stream (stream B in Table 13), and a tails stream (stream C in Table 13), corresponding to the gaseous overhead stream 41, the liquid side stream 42 and the tails stream 43 in FIG. 3, respectively, were withdrawn from the column.

The topping column comprised a packed column equivalent to about 60 theoretical plates. The base temperature of the topping column was maintained at about 179° C., the head temperature was maintained at about 150° C., and the temperature at theoretical plate 40 was maintained at about 175° C. The bottoms stream from column 14 was fed to about theoretical plate 40 of the topping column at a temperature of about 100° C. The topping column was operated at a pressure of about 400 mm measured at the top of the column. The R/D and D/F volume ratios in the topping column were maintained at about 150 and 0.014, respectively. A gaseous overhead stream, corresponding to the gaseous overhead stream 46B in FIG. 3, and a liquid bottoms stream (stream D in Table 13), corresponding to the liquid bottoms stream 47B in FIG. 3, were withdrawn from the topping column.

The refining column consisted of 35 trays and had liquid dividing heads at trays 35 and 25 for withdrawing a gaseous overhead stream of antifreeze grade ethylene glycol, corresponding to the gaseous overhead stream 48B in FIG. 3, and a liquid side stream (stream E in Table 13), corresponding to the liquid side stream 49B in FIG. 3, respectively. The liquid bottoms stream from the topping column was fed to the refining column at tray 10 at a temperature of about 170° C. The refining column was operated at a base temperature of about 165° C., a head temperature of about 156° C. and a column pressure of about 200 torr measured at the top of the column. Temperatures of 158° C. and 161° C., a were maintained at trays 25 and 10, respectively. An R/D ratio of about 10.0, and IR/LSS ratio of about 1.0, a D/F ratio of about 0.10, and an LSS/F ratio of about 0.68 were maintained in the refining column.

Ultraviolet transmittance measurements for the liquid side stream from the refining column (stream E in Table 13—the polyester-grade ethylene glycol stream) are reported below in Table 14.

TABLE 13

| Component | Composition Profiles Area Percent | | | | |
|---|---|---|---|---|---|
| | A | B | C | D | E |
| Water | 2.93 | 11.40 | 0.13 | 0.07 | 0.06 |
| Methanol | 29.76 | 6.83 | — | — | — |
| Ethanol | 1.31 | 0.36 | — | — | — |
| Methyl Glycolate | 0.35 | 9.00 | — | — | — |
| Ethylene Glycol | 64.35 | 53.24 | 99.02 | 99.43 | 99.70 |
| Dimethyl Oxalate | 0.07 | 0.14 | — | — | — |
| 1,2-Butanediol | 0.68 | 7.25 | 0.75 | 0.42 | 0.21 |
| Others | 0.55 | 11.03 | 0.10 | 0.06 | 0.03 |

TABLE 14

| Ultraviolet Transmittance, Percent Stream E of Table 13 | | |
|---|---|---|
| 350 nm | 275 nm | 220 nm |
| 100.0 | 98.2 | 82.0 |

Although certain embodiments of the invention have been described in detail, it will be appreciated that other embodiments are contemplated along with modifications of the disclosed features, as being within the scope of the invention, which is defined in the appended claims.

We claim:

1. A process for recovering polyester-grade ethylene glycol from crude ethylene glycol containing at least one component which has a normal boiling point below that of ethylene glycol, and which is capable of forming a UV absorber in the presence of ethylene glycol, comprising:

(a) adjusting the pH of a crude ethylene glycol stream to suppress the formation of UV absorbers by the addition of acid such that the determined pH of the crude ethylene glycol stream is in the range of from about 4.0 to about 7.5; and then (b) rectifying said pH adjusted crude ethylene glycol stream and recovering polyester-grade ethylene glycol in an ethylene glycol distillation system.

2. The process of claim 1 wherein said at least one component comprises dialkyl oxalate, alkyl glycolate or a mixture thereof.

3. The process of claim 1 wherein said at least one component comprises dimethyl oxalate, methyl glycolate or a mixture thereof.

4. The process of claim 3 wherein the dimethyl oxalate and methyl glycolate in said crude ethylene glycol stream together comprise at least about 0.05 percent by weight of said stream.

5. The process of claim 1 wherein said acid comprises phosphoric acids.

6. A process for recovering polyester-grade ethylene glycol from crude ethylene glycol containing dimethyl oxalate, methyl glycolate or a mixture thereof, which dimethyl oxalate, methyl glycolate or mixture thereof are capable of forming UV absorbers, comprising:

(a) adjusting the pH of a crude ethylene glycol stream to suppress the formation of UV absorbers by providing that the dimethyl oxalate and methyl glycolate in said crude ethylene glycol stream together comprise at least about 0.05 percent by weight of said stream such that the determined pH in said stream is in the range of from about 4.0 to about 7.5; and then (b) recovering polyester-grade ethylene glycol from said crude ethylene glycol stream in an ethylene glycol distillation system.

7. A process for recovering polyester-grade ethylene glycol from crude ethylene glycol containing at least one component which has a normal boiling point below that of ethylene glycol, and which can form a UV absorber in the presence of ethylene glycol comprising;

(a) feeding said crude ethylene glycol to a fractional distillation zone having an upper portion, a lower portion, and an intermediate portion;

(b) in said intermediate portion of said fractional distillation zone wherein at least ethylene glycol, said at least one component and a diluent having a normal boiling point below that of said at least one component and capable of being at least partially in a liquid phase in said intermediate portion are present, maintaining said diluent at a concentration sufficient to reduce formation of UV absorber in said intermediate portion; and (c) withdrawing a first stream from the lower portion of said fractional distillation zone, said first stream comprising ethylene glycol and being substantially free of said at least one component.

8. The process of claim 7 wherein said diluent comprises methanol.

9. The process of claim 8 wherein said at least one component comprises dimethyl oxalate, methyl glycolate or a mixture thereof.

10. The process of claim 9 wherein a second stream is withdrawn from said intermediate portion of said fractional distillation zone, said second stream comprising said at least one component.

11. The process of claim 10 wherein a third stream is withdrawn from the upper portion of said fractional distillation zone, said third stream comprising said diluent.

12. The process of claim 10 wherein a third stream comprising said methanol diluent is withdrawn from the upper portion of said fractional distillation zone.

13. The process of claim 12 wherein at least a portion of said third stream is condensed and returned to said fractional distillation zone.

14. A process for recovering polyester-grade ethylene glycol from a crude ethylene glycol containing methanol and at least one component which has a normal boiling point below that of ethylene glycol, and which can form a UV absorber in the presence of ethylene glycol comprising:
(a) feeding said crude ethylene glycol to a fractional distillation zone having an upper portion, a lower portion and an intermediate portion;
(b) supplying sufficient liquid methanol reflux to said upper portion to reduce the formation of UV absorber in said intermediate portion;
(c) withdrawing ethylene glycol substantially free of said at least one component from the lower portion of said fractional distillation zone; and
(d) withdrawing from said intermediate portion of the fractional distillation zone a stream containing said at least one component.

15. The process of claim 14 wherein said at least one component comprises dimethyl oxalate, methyl glycolate or a mixture thereof.

16. The process of claim 15 wherein methanol vapor is withdrawn from the upper portion of said fractional distillation zone.

17. The process of claim 16 wherein at least a portion of said methanol vapor is condensed and returned to said fractional distillation zone as said liquid methanol reflux.

18. The process of claim 15 wherein said crude ethylene glycol has a pH in aqueous solution of less than about 7.5.

19. A process for recovering polyester-grade ethylene glycol from a crude ethylene glycol containing methanol and dimethyl oxalate, methyl glycolate or a mixture thereof, comprising:
(a) feeding said crude ethylene glycol to a first fractional distillation zone having an upper portion and a lower portion;
(b) withdrawing ethylene glycol substantially free of dimethyl oxalate and methyl glycolate from the lower portion of said fractional distillation zone;
(c) withdrawing a stream containing methanol and dimethyl oxalate, methyl glycolate or a mixture thereof from the upper portion; and
(d) supply sufficient reflux liquid to the upper portion of the distillation zone to reduce the formation of UV absorber in said distillation zone.

20. The process of claim 19 wherein said crude ethylene glycol has a pH in aqueous solution of less than about 7.5.

* * * * *

UNITED STATES PATENT AND TRADEMARK OFFICE
CERTIFICATE OF CORRECTION

PATENT NO. : 4,830,712

DATED : May 16, 1989

INVENTOR(S) : John W. Crandall; Bernard C. Ream

It is certified that error appears in the above-identified patent and that said Letters Patent is hereby corrected as shown below:

Column 4, line 8, "were" should read --where--.

Column 5, line 16, "supported unsupported" should read --supported or unsupported--.

Column 6, line 52, "increase" should read --increased--.

Column 8, line 23, "facilities" should read --facilitates--.

Column 10, line 32, "separate" should read --separated--.

Column 11, line 27, "column 9" should read --column 90--.

Column 12, line 21, "time" should read --timer--.

Column 12, line 47, "preheated" should read --preheater--.

Column 12, line 55, "liquid-div-" should read --liquid-divid- --.

Column 12, line 56, "time" should read --timer--.

Column 12, line 59, "value" should read --valve--.

Column 13, line 26, "weighted" should read --weighed--.

UNITED STATES PATENT AND TRADEMARK OFFICE
CERTIFICATE OF CORRECTION

PATENT NO. : 4,830,712

DATED : May 16, 1989

INVENTOR(S) : John W. Crandall; Bernard C. Ream

It is certified that error appears in the above-identified patent and that said Letters Patent is hereby corrected as shown below:

Column 18, line 41, "reflex" should read --reflux--.

Column 21, line 22, "161°C., a" should read --161°C.--.

Claim 5, line 2, "acids" should read --acid--.

Signed and Sealed this

Eleventh Day of February, 1992

Attest:

HARRY F. MANBECK, JR.

*Attesting Officer*  *Commissioner of Patents and Trademarks*